United States Patent
Lynch (10) Patent No.: US 11,813,080 B2
(45) Date of Patent: Nov. 14, 2023

(54) SENSOR DEVICE, METHOD AND WEARABLE ARTICLE

(71) Applicant: PREVAYL INNOVATIONS LIMITED, Manchester (GB)

(72) Inventor: Michael John Lynch, Manchester (GB)

(73) Assignee: PREVAYL INNOVATIONS LIMITED, Manchester (GB)

( * ) Notice: Subject to any disclaimer, the term of this patent is extended or adjusted under 35 U.S.C. 154(b) by 0 days.

(21) Appl. No.: 17/779,481

(22) PCT Filed: Nov. 26, 2020

(86) PCT No.: PCT/GB2020/053015
§ 371 (c)(1),
(2) Date: May 24, 2022

(87) PCT Pub. No.: WO2021/105685
PCT Pub. Date: Jun. 3, 2021

(65) Prior Publication Data
US 2023/0010116 A1    Jan. 12, 2023

(30) Foreign Application Priority Data

Nov. 28, 2019 (GB) ..................................... 1917334

(51) Int. Cl.
*A61B 5/00* (2006.01)
*A61B 5/02* (2006.01)
*H04L 5/14* (2006.01)

(52) U.S. Cl.
CPC .............. *A61B 5/6802* (2013.01); *A61B 5/02* (2013.01); *A61B 5/6803* (2013.01); *A61B 5/6804* (2013.01); *H04L 5/14* (2013.01)

(58) Field of Classification Search
CPC ........... A61B 5/00; A61B 5/0002; A61B 5/01; A61B 5/02007; A61B 5/02055;
(Continued)

(56) References Cited

U.S. PATENT DOCUMENTS 6,646,336 B1    11/2003    Marmaropoulos et al.
6,943,061 B1    9/2005     Sirinorakul et al.
(Continued)

FOREIGN PATENT DOCUMENTS

CN    110123305 A    8/2019
DE    19647668 A1    5/1998
(Continued)

OTHER PUBLICATIONS

NPL Search (Apr. 6, 2023).*
(Continued)

*Primary Examiner* — Van T Trieu
(74) *Attorney, Agent, or Firm* — Haley Guiliano LLP (57) ABSTRACT

The sensor device (10) comprises a sensor module (101) and an input-output interface (105) arranged to send and receive data over a bidirectional line (11). A buffer (103) is arranged to store time-series sensor data. A programmable and erasable nonvolatile memory (109) receives and stores an identifier for the sensor device (10). The sensor module (101) generates an inference using the sensor data. The sensor device (10) is arranged to switch between sending, over the bidirectional line (11), data sensed by the sensor module (101) and the generated inference. The sensor device (10) is a single-wire sensor device. The input-output interface (105) is a single-wire input-output interface. The sensor module (101) is a motion, electropotential, electroimpedance, chemical, or optical sensor module. The sensor device (10) is provided in a system comprising a master device. The sensor device (10) or system is incorporated into a wearable article.

15 Claims, 3 Drawing Sheets

(58) Field of Classification Search
CPC ....... A61B 5/026; A61B 5/031; A61B 5/1118;
A61B 5/412; A61B 5/418; A61B 5/6802;
A61B 5/6887; G08C 19/00; G01D 9/00;
G01D 9/005; G01D 21/00; H04L 5/14
See application file for complete search history.

(56) References Cited

U.S. PATENT DOCUMENTS

| | | | |
|---|---|---|---|
| 8,022,522 B1 | 9/2011 | Liou et al. | |
| 9,138,191 B1 | 9/2015 | Kaskoun et al. | |
| 11,534,615 B2* | 12/2022 | Briscoe | A61B 5/7455 |
| 11,571,143 B2* | 2/2023 | Katz | A61B 5/1118 |
| 2003/0023777 A1 | 1/2003 | Fields et al. | |
| 2003/0211797 A1 | 11/2003 | Hill et al. | |
| 2007/0152812 A1 | 5/2007 | Wong et al. | |
| 2007/0164409 A1 | 7/2007 | Holland | |
| 2007/0173083 A1 | 7/2007 | Kopplin | |
| 2007/0214872 A1 | 9/2007 | Ammann et al. | |
| 2010/0036209 A1* | 2/2010 | Ferren | A61B 5/4839 600/301 |
| 2014/0070957 A1 | 3/2014 | Longinotti-Buitoni | |
| 2014/0135593 A1 | 5/2014 | Jayalth et al. | |
| 2014/0269812 A1 | 9/2014 | Deutscher et al. | |
| 2015/0015249 A1 | 1/2015 | Ausserlechner et al. | |
| 2017/0053856 A1 | 2/2017 | Luan | |
| 2017/0181703 A1 | 6/2017 | Kaib et al. | |
| 2017/0264978 A1 | 9/2017 | Leftly et al. | |
| 2018/0090449 A1 | 3/2018 | Jeong et al. | |
| 2018/0107244 A1 | 4/2018 | Fujie et al. | |
| 2018/0138616 A1 | 5/2018 | Dumont | |
| 2018/0184975 A1 | 7/2018 | Kaasinen et al. | |
| 2018/0295720 A1 | 10/2018 | Aleksov et al. | |
| 2019/0076082 A1 | 3/2019 | Poutiatine et al. | |
| 2019/0133474 A1 | 5/2019 | Longinotti-Buitoni | |
| 2019/0166089 A1 | 5/2019 | Schmitz et al. | |
| 2022/0384315 A1 | 12/2022 | Lynch | |

FOREIGN PATENT DOCUMENTS

| | | |
|---|---|---|
| DE | 10251900 A1 | 5/2004 |
| EP | 3370367 A1 | 9/2018 |
| GB | 2555592 A | 5/2018 |
| GB | 2589567 A | 6/2021 |
| GB | 2592391 A | 9/2021 |
| GB | 2593479 A | 9/2021 |
| GB | 2593674 A | 10/2021 |
| WO | 2011095857 A1 | 8/2011 |
| WO | 2016051268 A1 | 4/2016 |
| WO | 2016054057 A1 | 4/2016 |
| WO | 2019020550 A2 | 1/2019 |
| WO | 2019134031 A2 | 7/2019 |
| WO | 2019197892 A1 | 10/2019 |
| WO | 2021105676 A1 | 6/2021 |

OTHER PUBLICATIONS

British Search Report, dated Aug. 6, 2020, issued in GB Pat. App. No. 1917332.7 (4 pages).
British Search Report, dated Aug. 19, 2020, issued in GB Pat. App. No. 1917334.3 (3 pages).
British Search Report, dated Mar. 10, 2021, issued in GB Pat. App. No. 1917342.6 (4 pages).
"Datasheet DS2422", Maxim Integrated, 2010, pp. 1-49, retrieved from the Internet: URL: https://datasheets.maximintegrated.com/en/ds/DS2422.pdf [retrieved on Jul. 24, 2017].
International Search Report and Written Opinion, dated Feb. 25, 2021, issued in Int'l. App. No. PCT/GB2020/053015 (9 pages).
International Search Report and Written Opinion, dated Feb. 26, 2021, issued in Int'l. App. No. PCT/GB2020/053006 (17 pages).
International Search Report and Written Opinion, dated Apr. 7, 2021, issued in Int'l. App. No. PCT/GB2020/053010 (23 pages).
International Search Report and Written Opinion, dated Apr. 7, 2021, issued in Int'l. App. No. PCT/GB2020/053012 (24 pages).
Silicon Labs: "I2C Humidity and Temperature Sensor", pp. 1-36, Aug. 1, 2016, retrieved from the Internet: URL: https://cdn-learn.adafruit.com/assets/assets/000/035/931/original/Support_Documents_technicalDocs_Si7021-A20.pdf [retrieved on Jun. 5, 2019].
Chew, et al., "Electrical Power Monitoring System Using Thermochron Sensor and 1-Wire Communication Protocol", 4th IEEE International Symposium on Electrical Design, pp. 549-554 (2008).
Examination Report received in GB2002716.5 dated Jun. 30, 2022.
Examination Report received in GB2002716.5 dated Mar. 18, 2022.
Examination Report received in GB2002716.5 dated Mar. 23, 2021.
Examination Report received in GB2002716.5 dated Mar. 9, 2021.
Examination Report received in GB2002716.5 dated May 16, 2022.
GB Search Report dated Apr. 6, 2020 of GB Application 1917331.9.
GB Search Report dated Sep. 16, 2020 of GB Application 2004244.6.
GB Search Report dated Sep. 16, 2020 of GB Application 2004245.3.
International Search Report and Written Opinion of PCT/GB2020/053005 dated Feb. 22, 2021.
International Search Report and Written Opinion received for PCT Patent Application No. PCT/GB2020/053006, dated Feb. 26, 2021, 14 pages.
International Search Report and Written Opinion, dated Feb. 18, 2021, issued in Int'l. App. No. PCT/GB2020/053009 (15 pages).
International Search Report received in PCT/GB2021/050449 dated May 11, 2021.
Search and Examination Report received in GB2002716.5 dated Aug. 18, 2020.
Search Report received in GB2002717.3 dated Aug. 17, 2020.
Written Opinion received in PCT/GB2021/050449 dated May 11, 2021.
U.S. Appl. No. 17/772,242, filed Apr. 27, 2022, Michael John Lynch.
U.S. Appl. No. 17/779,483, filed May 24, 2022, Michael John Lynch.
U.S. Appl. No. 17/779,486, filed May 24, 2022, Michael John Lynch.
U.S. Appl. No. 17/796,949, filed Aug. 2, 2022, Michael John Lynch.

* cited by examiner

SENSOR DEVICE, METHOD AND WEARABLE ARTICLE

CROSS-REFERENCE TO RELATED APPLICATIONS

This application is a national stage application under 35 U.S.C. § 371 of International Application PCT/GB2020/053015, filed Nov. 26, 2020, which claims priority of GB Patent Application 1917334.3, filed Nov. 28, 2019. The disclosure of which are hereby incorporated by reference herein in their entireties.

BACKGROUND

The present invention is directed towards a sensor device, wearable article, system and method. Sensor devices can communicate with one or more master devices over a serial protocol. Example serial protocols include Serial Peripheral Interface (SPI), Inter-Integrated Circuit (I2C), Controller Area Network (CAN), and Recommended Standard 232 (RS-232). In these and other example protocols, many sensor devices may be connected to the master device over one or more shared communication lines. Beneficially, this reduces the number of physical communication lines which can reduce the cost and complexity of the resultant sensor system. This is particularly advantageous for wearable articles such as garments as having many communication lines can reduce the comfort and physical appearance of the wearable article.

One problem with shared communication lines is that each sensor device only has a limited time access to the communication lines for sending data to the master device. This means that data communicated to the master device may have a lower sampling rate than the available sampling rate of the sensor device.

Another problem with shared communication lines is that each sensor device may have a unique, unalterable, factory-programmed identifier. This increases the burden on the master device as the master device has to obtain these identifiers prior to performing communication with the sensor devices and increases the risk of error due to the use of an incorrect identifier.

Yet another problem is that even if the sensor device uses a shared communication line, the sensor devices may still require separate power lines to ensure a consistent power supply. This increases the number of physical conductors required which is a problem for wearable articles.

SUMMARY

According to the present disclosure there is provided a sensor device, wearable article, system and method as set forth in the appended claims. Other features of the invention will be apparent from the dependent claims, and the description which follows.

According to a first aspect of the present disclosure, there is provided a sensor device. The sensor device comprises a sensor module. The sensor device comprises a buffer arranged to store time-series sensor data sensed by the sensor module. The sensor device comprises an input-output interface arranged to send and receive data over a bidirectional line.

The sensor device is therefore arranged to store time series sensor data in a buffer. This allows the sensor device to temporarily store data prior to transmission over the input-output interface. This is beneficial as the sensor device is generally only able to transmit data over the bidirectional line for a limited period of time. This is because the sensor device is unable to transmit data over the bidirectional line when other devices such as other sensor devices or a master device are utilising the bidirectional line bus for data transmission. The buffer therefore enables the sensor device to locally store time-series sensor data until a command is received from a master device for transmitting data over the input-output interface.

The time series sensor data stored in the buffer may comprise 2 or more samples of sensor data, 5 or more samples of sensor data, 10 or more samples of sensor data, 50 or more samples of sensor data, 100 or more samples of sensor data, 500 or more samples of sensor data, or 1000 or more samples of sensor data. The buffer may be arranged to store up to or more than 10 minutes of data sensed by the sensor module, up to or more than 30 minutes of data sensed by the sensor module, up to or more than 1 hour of data sensed by the sensor module, up to or more than 6 hours of data sensed by the sensor module, up to or more than 12 hours of data sensed by the sensor module, up to or more than 24 hours of data sensed by the sensor module, up to or more than 1 week of data sensed by the sensor module, or up to or more than 1 month of data sensed by the sensor module. The buffer may have a storage capacity of at least 500 bytes, at least one 1 kilobyte, at least 5 kilobytes, at least 50 kilobytes, at least 500 kilobytes, at least 1 megabyte, at least 5 megabytes, at least 50 megabytes, at least 60 megabytes, at least 100 megabytes, at least 200 megabytes, or at least 250 megabytes. It will be appreciated that there is no required upper limit to the storage capacity of the buffer particularly considering the continual development in memory devices. At the time of writing, it may be desirable that the buffer does not have a storage capacity of more 8 gigabytes due to physical size considerations when integrating the sensor device in a wearable article such as a garment. However, it will be appreciated that as the physical size of storage devices decreases buffers with larger storage capacities may be able to be integrated into the wearable article.

The input-output interface may be arranged to send the time-series sensor data over the bidirectional line. The input-output interface may be arranged to send the data in response to receiving a request for data from a master device over the bidirectional line. Advantageously, this approach enables a master device to request and read data from the buffer of the sensor device.

The input-output interface may be a single-wire input-output interface. The bidirectional line may be a single-wire bidirectional line. The use of a single-wire protocol means that only one-wire is used to send and receive data over the sensor device. Beneficially, this is the minimum possible number of conductive lines that may be provided. This reduces the number of physical hardware connections required for data transmission to/from the sensor device and is particularly beneficial for wearable article implementations. It is appreciated that even with a single-wire protocol, a separate ground line may still be provided. The present disclosure is not limited to single-wire input-output interfaces and single-wire bidirectional lines although particular advantages are achieved in these examples. Two-wire bidirectional lines, three-wire bidirectional lines or four or more wire bidirectional lines may also be used in some examples. The bidirectional lines may use any existing serial protocol such as Serial Peripheral Interface (SPI), Inter-Integrated Circuit (I2C), Controller Area Network (CAN), Recommended Standard 232 (RS-232), and 1-wire The sensor device may be arranged to receive power via the input-output interface. Advantageously, this enables the sensor device to be powered without requiring separate power lines. The bidirectional line may therefore be used for both communication and power. The sensor device may further comprise a power source arranged to supply power to the sensor device. Beneficially, the power source helps ensure that a consistent power supply is provided for the sensor device without requiring separate power lines. The sensor device may be arranged to receive power over the input-output interface and store the power in the power source. This enables sensor devices to be consistently powered even when the bidirectional line is shared by many devices which generally means that the sensor device only has a limited time window to receive power over the bidirectional line. The power source may comprise a capacitor. The capacitor may be a supercapacitor. The power source may comprise a rechargeable battery.

The sensor device may further comprise a non-volatile memory arranged to store an identifier for the sensor device. The non-volatile memory may be a read-only memory. The memory may be a programmable non-volatile memory such as a programmable read-only memory (PROM). The memory may be is an erasable and reprogrammable non-volatile memory such as an erasable programmable read-only memory (EPROM), and electrically erasable programmable read-only memory (EEPROM) or a floating-gate memory such as flash memory. The input-output interface may be arranged to receive an identifier over the bidirectional line and write the identifier to the erasable and programmable memory. Advantageously, the programmable and erasable non-volatile memory allows for the identifiers to be changed or adapted by a master device coupled to the sensor device as desired. In this way, the burden on the master device and the risk of error is reduced.

The input-output interface may be arranged to receive an identifier over the bidirectional line. The sensor device may be arranged to compare the received identifier to an identifier stored in the non-volatile memory.

The sensor module may comprise a processor and a memory. The memory may store instructions. The instructions when executed by the processor may cause the processor to perform operations, the operations comprising generating a compressed representation of data sensed by the sensor module. The compressed representation may comprise an inference generated from data sensed by the sensor module. The processor may generate the inference by employing a machine-learned model stored on the memory of the sensor module.

The input-output interface may be arranged to send the compressed representation of the data sensed by the sensor module over the bidirectional line. Advantageously, the sensor device may be arranged to transmit the compressed representation of the data over the bidirectional line for real-time or near-real time applications, while still storing the sensor data in the buffer for later transmission and analysis.

The sensor device may be arranged to switch between sending, over the bidirectional line via the input-output interface, the time series data sensed by the sensor module and the compressed representation of data sensed by the sensor module. The sensor device may be arranged to switch in response to a command received from the master device over the bidirectional line. This enables the sensor device to change the type of data being output by the sensor device based on factors such as whether real-time data is required by the master device. Real-time, low resolution, data may be required for real-time data visualisation applications, while the time series data sensed by the sensor module may be required for offline analysis such as for use in training machine-learned models.

The sensor module may comprise one or more of a temperature sensor module, a humidity sensor module, a motion sensor module, an electropotential sensor module, an electroimpedance sensor module, an optical sensor module, an acoustic sensor module. The temperature sensor module may be arranged to measure an ambient temperature, a skin temperature of a human or animal body, or a core temperature of a human or animal body. The humidity sensor module may be arranged to measure humidity or skin-surface moisture levels for a human or animal body. The motion sensor module may comprise one or more of an accelerometer, a gyroscope, and a magnetometer sensor module. The motion sensor module may comprise an inertial measurement unit. The electropotential sensor module may be arranged to perform one or more bioelectrical measurements. The electropotential sensor module may comprise one or more of electrocardiography (ECG) sensor modules, electrogastrography (EGG) sensor modules, electroencephalography (EEG) sensor modules, and electromyography (EMG) sensor modules. The electroimpedance sensor module may be arranged to perform one or more bioimpedance measurements. Bioimpedance sensor modules can include one or more of plethysmography sensor modules (e.g., for respiration), body composition sensor modules (e.g., hydration, fat, etc.), and electroimpedance tomography (EIT) sensor modules. An optical sensor module may comprise a photoplethysmography (PPG) sensor module or an orthopantomogram (OPG) sensor module. The sensor module comprises one or more biosensor (e.g. biosignal sensing) modules.

According to a second aspect of the present disclosure, there is provided a method. The method comprises providing a sensor device comprising a sensor module, a buffer, and an input-output interface. The method comprises controlling the buffer to store time-series sensor data sensed by the sensor module in the buffer. The method comprises controlling the input-output interface to send and receive data over a bidirectional line. The method may further comprise controlling the input-output interface to send the time-series sensor data over the bidirectional line.

According to a third aspect of the present disclosure, there is provided a single-wire sensor device. The sensor device comprises a sensor module. The sensor device comprises a programmable and erasable non-volatile memory. The sensor device comprises a single-wire input-output interface arranged to send and receive data over a single-wire bidirectional line. The single-wire input-output interface may be arranged to receive an identifier over the single-wire bidirectional line and write the identifier to the programmable and erasable non-volatile memory.

Advantageously, the sensor device uses a single-wire bidirectional line for communicating data. This is the minimum possible number of communication lines and thus minimizes the number of physical conductors required which is particularly beneficial for wearable articles. The sensor device has a programmable and erasable non-volatile memory which stores an identifier for the sensor device. The programmable and erasable non-volatile memory enables the identifier to be changed and thus provides for greater flexibility in controlling how the sensor device is addressed.

According to a fourth aspect of the present disclosure, there is provided a method. The method comprises providing a single-wire sensor device comprising a sensor module, a programmable and erasable non-volatile memory, and a single-wire input-output interface. The method comprises controlling the single-wire input-output interface to receive an identifier over a single-wire bidirectional line and write the identifier to the programmable and erasable non-volatile memory. The method comprises controlling the single-wire input-output interface to send and receive data over the single-wire bidirectional line.

According to a fifth aspect of the present disclosure, there is provided a sensor device. The sensor device comprises a sensor module. The sensor device comprises an input-output interface arranged to send and receive data over a bidirectional line. The sensor module comprises a processor and a memory, wherein the memory stores instructions, and wherein the instructions when executed by the processor cause the processor to perform operations, the operations comprising generating an inference using data sensed by the sensor module. The sensor device is arranged to switch between sending, over the bidirectional line via the input-output interface, data sensed by the sensor module and the inference generated by the sensor.

Advantageously, the sensor device is able to switch between outputting an inference and the data sensed by the sensor module. The inference may be output when data is needed for real-time or near real-time analysis. The data sensed by the sensor module may be output when real-time analysis is no longer required. The data sensed by the sensor module may be useful for offline analysis such as for use in the training of machine-learned models.

According to a sixth aspect of the present disclosure, there is provided a single-wire motion sensor. The singe-wire motion sensor device comprises a motion sensor module; a power source arranged to supply power to the sensor device; and a single-wire input-output interface arranged to send and receive data over a single-wire bidirectional line. The sensor device is arranged to receive power over the single-wire input-output interface and store the power in the power source.

Advantageously, there is provided a motion sensor which only uses a single-wire bidirectional line for sending and receiving data and also for receiving power. No other communication lines or power lines are provided for the motion sensor. A ground line may still be provided. The motion sensor therefore has the minimum possible number of physical communication and power lines which is particularly beneficial for wearable articles. Since a single-wire bidirectional line is used for data and power, the motion sensor may not be provided with a consistent supply of power. The power source of the motion sensor is advantageously provided to overcome this issue.

According to a seventh aspect of the present disclosure, there is provided a single-wire electropotential sensor device. The single-wire electropotential sensor comprises an electropotential sensor module; a power source arranged to supply power to the sensor device; and a single-wire input-output interface arranged to send and receive data over a single-wire bidirectional line. The sensor device is arranged to receive power over the single-wire input-output interface and store the power in the power source.

According to an eighth aspect of the present disclosure, there is provided a single-wire electroimpedance sensor. The sensor comprises an electroimpedance sensor module a power source arranged to supply power to the sensor device; and a single-wire input-output interface arranged to send and receive data over a single-wire bidirectional line. The sensor device is arranged to receive power over the single-wire input-output interface and store the power in the power source.

According to a ninth aspect of the present disclosure, there is provided a single-wire chemical (e.g. biochemical) sensor. The single-wire chemical sensor comprises a chemical sensor module; a power source arranged to supply power to the sensor device; and a single-wire input-output interface arranged to send and receive data over a single-wire bidirectional line. The sensor device is arranged to receive power over the single-wire input-output interface and store the power in the power source.

According to a tenth aspect of the present disclosure, there is provided a single-wire optical sensor. The single-wire optical sensor comprises an optical sensor module; a power source arranged to supply power to the sensor device; and a single-wire input-output interface arranged to send and receive data over a single-wire bidirectional line. The sensor device is arranged to receive power over the single-wire input-output interface and store the power in the power source.

According to an eleventh aspect of the present disclosure, there is provided a wearable article comprising the sensor device as described above in relation to the first, third, fifth, sixth, seventh, eighth, ninth or tenth aspect of the present disclosure.

According to a twelfth aspect of the present disclosure, there is provided a system. The system comprises a master device. The system comprises a sensor device as described above in relation to the first, third, fifth, sixth, seventh, eighth, ninth or tenth aspect of the present disclosure. The sensor device and the master device are connected to one another over a bidirectional line. Data is able to be exchanged between the master device and the sensor device over the bidirectional line.

According to a thirteenth aspect of the present disclosure, there is provided a wearable article. The wearable article comprises the system according to the twelfth aspect of the present disclosure. The master device may be releasably coupled to the wearable article.

According to a fourteenth aspect of the present disclosure, there is provided a wearable article. The wearable article comprises a single-wire bidirectional line. The wearable article comprises a plurality of single-wire sensor devices. Each of the sensor devices comprises a sensor module; and a single-wire input-output interface arranged to send and receive data over the single-wire bidirectional line.

According to a fifteenth aspect of the present disclosure, there is provided a wearable article. The wearable article comprises a master device releasably attached to the wearable article. The wearable article comprises a single-wire bidirectional line. The wearable article comprises a sensor device. The sensor device comprises a sensor module; and a single-wire input-output interface arranged to send and receive data over the single-wire bidirectional line. The master device is connected to the sensor device using the single-wire bidirectional line.

According to a sixteenth aspect of the present disclosure, there is provided a single-wire sensor device comprising: a sensor module; and a single-wire input-output interface arranged to send and receive data over a single-wire bidirectional line, wherein the sensor module comprises a processor and a memory, wherein the memory stores instructions, and wherein the instructions when executed by the processor cause the processor to perform operations, the operations comprising generating an inference using data sensed by the sensor module. The single-wire sensor device may be useable in any of the aspects of the present disclosure.

Any one aspect of the present disclosure may comprise the features of any other aspect of the present disclosure.

The present disclosure is not limited to wearable articles. The sensor devices and systems disclosed herein may be incorporated into other forms of devices such as user electronic devices (e.g. mobile phones). In additions, the sensor devices and system disclosed herein may be incorporated into any form of textile article. Textile articles may include upholstery, such as upholstery that may be positioned on pieces of furniture, vehicle seating, as wall or ceiling décor, among other examples.

BRIEF DESCRIPTION OF THE DRAWINGS

Examples of the present disclosure will now be described with reference to the accompanying drawings, in which.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

"Wearable article" as referred to throughout the present disclosure may refer to any form of electronic device which may be worn by a user such as a smart watch, necklace, bracelet, or glasses. The wearable article may be a textile article. The wearable article may be a garment. The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, swimwear, wetsuit or drysuit The wearable article/garment may be constructed from a woven or a non-woven material. The wearable article/garment may be constructed from natural fibres, synthetic fibres, or a natural fibre blended with one or more other materials which can be natural or synthetic. The yarn may be cotton. The cotton may be blended with polyester and/or viscose and/or polyamide according to the particular application. Silk may also be used as the natural fibre. Cellulose, wool, hemp and jute are also natural fibres that may be used in the wearable article/garment. Polyester, polycotton, nylon and viscose are synthetic fibres that may be used in the wearable article/garment. The garment may be a tight-fitting garment. Beneficially, a tight-fitting garment helps ensure that the sensor devices of the garment are held in contact with or in the proximity of a skin surface of the wearer. The garment may be a compression garment. The garment may be an athletic garment such as an elastomeric athletic garment.

Figure 1:
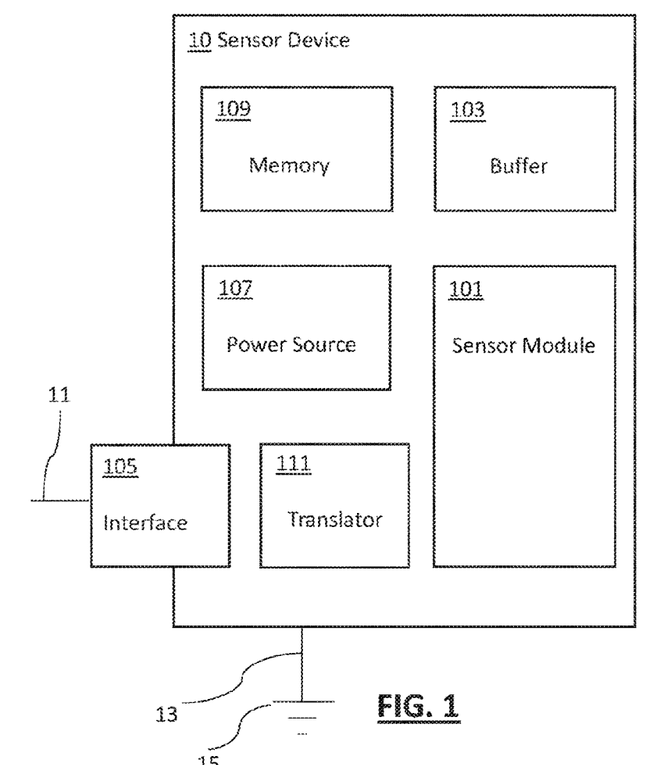
FIG. 1 shows a schematic diagram for an example sensor device according to aspects of the present disclosure.

Referring to FIG. 1, there is shown an example sensor device 10 according to aspects of the present disclosure. The sensor device 10 may comprise a number of electronics components 101, 103, 105, 107, 109, 111 provided within a semiconductor package. The electronics components comprise a sensor module 101, buffer 103, input-output (I/O) interface 105, power source 107, memory 109, and translator 111. The sensor device 10 is connected to a bidirectional communication line 11 via the input-output interface 105. The sensor device 10 is also connected to ground 15 via a ground line 13. The components of the sensor device 10 ma all be provided on the substrate. Therefore, a single integrate circuit may be provided containing all of the electronic components of the sensor device 10. The sensor device 10 may be provided in a single semiconductor package.

In the example of FIG. 1, the I/O interface is a single-wire bus interface and the bidirectional communication line 11 is a single-wire bidirectional line. The single-wire bidirectional line may be referred to as a one-wire bus, 1-wire, SDQ™, or a single-wire serial interface. The sensor device 10 may be referred to as a single-wire device. The use of a single-wire bidirectional line means that only one-wire is used to send and receive data over the sensor device 10. This reduces the number of physical hardware connections required for data transmission to/from the sensor device 10 to the minimum possible number. While there is a 1-wire electrical interface to the sensor, the physical cabling running through the garment may be doubled (or tripled etc.) up to improve reliability. That is, many wires in the garment may terminate at the same 1-wire electrical interface. This is beneficial for military, safety-critical or potential medical applications.

The sensor module 101 is arranged to sense data. The sensed data is temporarily stored in the buffer 103 prior to transmission of the data over the single-wire bidirectional line 11 connected to the I/O interface 105. The use of a buffer 103 is beneficial as the sensor device 10 is generally only able to transmit data over the single-wire bidirectional line 11 for a limited period of time. This is because the sensor device 10 is unable to transmit data over the single-wire bidirectional line 11 when other devices such as other sensor devices 10 or a master device are utilising the single-wire bidirectional line 11 for data transmission. The buffer 103 therefore enables the sensor device 10 to locally store time-series sensor data until a command is received from a master device for transmitting data over the I/O interface 105.

The sensor device 10 may be supplied with power over the single-wire bidirectional line 11. However, power may only be available during idle periods of the single-wire bidirectional line 11 when data is not being transmitted over the single-wire bidirectional line 11. To ensure consistent supply of power to the electronics components of the sensor device 10, the sensor device 10 comprises a power source 107. The power source 107 supplies power to the electronics components of the sensor device 10 even when power is not able to be source from the single-wire bidirectional line 11. During idle periods, the power source 107 may be charged over the single-wire bidirectional line 11. In some examples, the power source 107 is a capacitor such as a super capacitor. In some examples, the power source 107 is a rechargeable battery. Beneficially, the power source 107 enables the sensor device 10 to derive power from the single-wire bidirectional line 105, which means that an external power supply is not required for the sensor device 10. The absence of an external power supply reduces the number of physical connections required for the sensor device 10 and enables the sensor device 10 to be more seamless integrated into wearable articles.

The memory 109 of the sensor device 10 is arranged to store an identifier for the sensor device 10. The identifier may be a serial number for the sensor device 10. The identifier for the sensor device 10 may act as a device address and may enable the sensor device 10 to be individually selected from among a plurality of slave devices connected to the single-wire bidirectional line 11. The identifier may be in a global unique address format which may comprise a family code that identifies the device type, an individual address, and cyclic redundancy check (CRC) value. The CRC value enables the master device to determine if an address was read without error. Of course, other identifier formats may be used as appropriate by the skilled person in the art.

In some examples, the memory 109 is a non-volatile memory such as a read-only memory (ROM). In these examples, the identifier is written to the ROM memory 109 during manufacture of the sensor device 10 and is not changeable thereafter. The memory 109 may be a programmable non-volatile memory such as a programmable ROM (PROM). In these examples, the identifier may be written to the PROM memory 109 after the manufacture of the sensor device 10. This provides more flexibility in setting the identifiers for the memory 109. Preferred examples use an erasable and reprogrammable non-volatile memory 109 to allow for the content of the memory 109 to be changed and added to as desired. This allows for the identifiers to be changed or adapted based on factors such as the type of master device, and the number and type of slave devices connected to the single-wire bidirectional line 11. Examples of erasable and reprogrammable non-volatile memory include erasable programmable read-only memory (EPROM), electrically erasable programmable read-only memory (EEPROM) and floating-gate memory such as flash memory.

The translator 111 manages the flow of data to and from the sensor device 10 and controls the interaction between the sensor module 101, memory 109, and buffer 103. The translator 111 may also be known as a memory controller or one-wire port.

Figure 2:
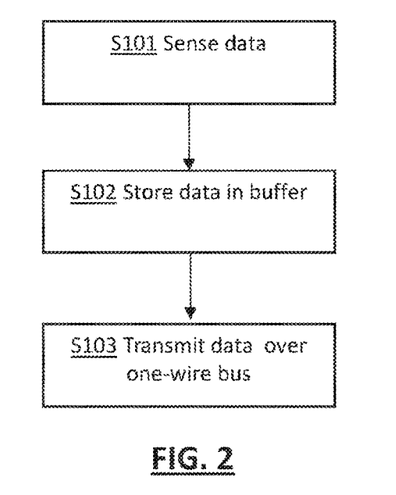
FIG. 2 shows a flow diagram for an example method according to aspects of the present disclosure.

Referring to FIG. 2, there is shown a flow diagram for an example method according to aspects of the present disclosure performed using the sensor device 10 of FIG. 1. Step S101 of the method comprises the sensor module 101 sensing data. In step S102, the sensed data is stored in the buffer 103. Steps S101 and S102 may be repeated for a plurality of iterations such that data representing a plurality of different time instances are written to the buffer 103. In other words, time series sensor data is stored in the buffer 103. In step S103, the data is read from the buffer 103 and transmitted over the single-wire bidirectional line 11 via the I/O interface 105. The data may be transmitted from the buffer 103 in response to receiving a command from a master device connected to the sensor device 10 over the single-wire bidirectional line 11. The sensor module 101 may continue to sense data and write the data to the buffer 103 as data is being read from the buffer 103. Beneficially, this method allows for a single-wire bidirectional line 11 to be used to transmit and receive data from the sensor device 10 without any loss of sensor data during time periods where the single-wire bidirectional line 11 is occupied and not able to be used to transmit data by the sensor module 10.

Figure 3:
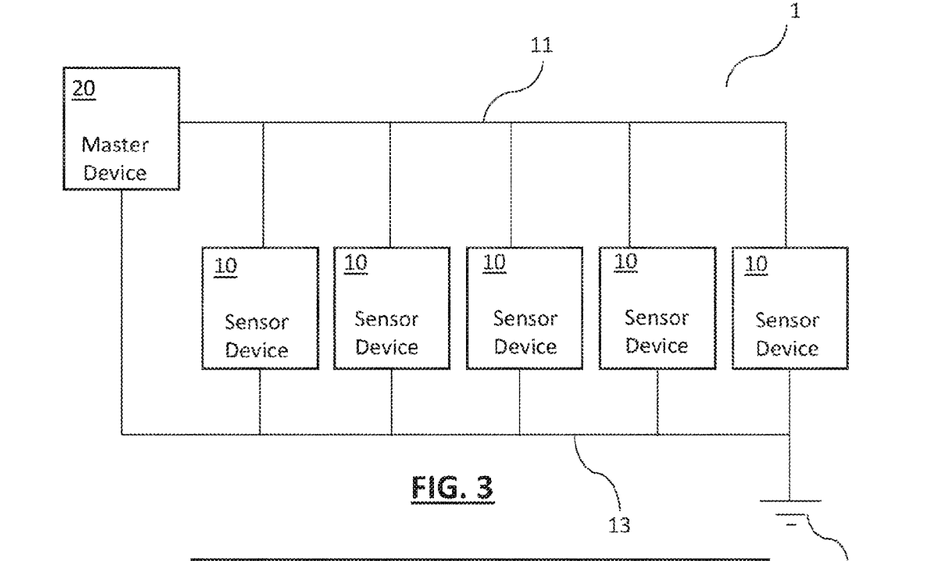
FIG. 3 shows a schematic diagram for an example system according to aspects of the present disclosure.

Referring to FIG. 3, there is shown a schematic diagram of an example system 1 comprising a master device 20 connected to a plurality of slave devices 10 using a single-wire bidirectional line 11. The plurality of slave devices 10 are sensor devices 10 as per the example sensor device 10 shown in FIG. 1. Each of the sensor devices 10 may comprise the same type of sensor module 101 or may comprise different types of sensor module 101 for sensing different types of data. Additional slave devices having different configurations to the sensor device 10 of FIG. 1 may also be connected to the single-wire bidirectional line 11. The plurality of sensor devices 10 and the master device 20 also have a ground line 13 for connecting the sensor devices 10 and master device 20 to ground 15. No other wired connections between the master device 20 and the sensor devices 10 are provided.

The master device 20 initiates the sensor devices 10 and controls the transmission of data over the single-wire bidirectional line 11. The master device 20 is arranged to transmit data to the sensor devices 10 and receive data from the sensor devices 10 over the single-wire bidirectional line 11. Power may also be transferred to the sensor devices 10 over the single-wire bidirectional line 11.

In an example operation, the master device 20 first transmits a "reset" command to the sensor devices 10 which synchronises all of the devices connected to the single-wire bidirectional line 11. The master device 20 then transmits a selection command comprising an identifier for one of the sensor devices 10 to the sensor devices 10 over the single-wire bidirectional line 11. The sensor device 10 with the corresponding identifier stored in the memory of the sensor device 10 is selected while the other sensor devices 10 configure themselves to ignore subsequent communications over the single-wire bidirectional line 11 until the next "reset" command is transmitted by the master device 20 over the single-wire bidirectional line 11.

Once the master device 20 has selected a particular sensor device 10, the master device 20 is able to transmit commands to the sensor device 10 as well as data to the sensor device 10. The master device 20 is also able to read data from the sensor device 10. The master device 20 may read data from the buffer of the sensor device 10. This enables the master device 20 to read time-series data from the buffer of the sensor device 10. The master device 20 may write data to the memory of the sensor device 10. The data written to the memory of the sensor device 10 may be a new or updated identifier for the sensor device 10. The master device 20 may transmit a command to the sensor device 10. The command may be for changing the type of data sensed by the sensor device 10 or the type of data output by the sensor device 10 over the single-wire bidirectional line 11.

In some situations, it may be desirable to provide data to the master device 20 in real-time or near real time. The master device 20 is able to transmit a request for recent data sensed by the sensor device 10, and the sensor device 10 transmits the recent data as a result. Meanwhile, the sensor device 10 may still retain data locally on the buffer. Once the master device 20 no longer requires real-time or near-real time data, the master device 20 may read out the original high resolution time-series sensor data from the buffer of the sensor device 10. This approach enables the master device 20 to obtain low-resolution data or data at a low sampling rate for real-time processing operations while still maintaining the original high-resolution/high sampling rate data for later retrieval and analysis.

The master device 20 may be a removable electronic module for the wearable article. The electronic module may be configured to be releasably mechanically coupled to the wearable article. The mechanical coupling of the electronic module to the wearable article may be provided by a mechanical interface such as a clip, a plug and socket arrangement, etc. The mechanical coupling or mechanical interface may be configured to maintain the electronic module in a particular orientation with respect to the garment when the electronic module is coupled to the wearable article. This may be beneficial in ensuring that the electronic module is securely held in place with respect to the garment and/or that any electronic coupling of the electronic module and the wearable article (or a component of the garment) can be optimized.

The mechanical coupling may be maintained using friction or using a positively engaging mechanism, for example.

Beneficially, the removable electronic module may contain all of the components required for data transmission and processing such that the wearable article only comprises the sensor devices and the bidirectional line. In this way, manufacture of the wearable article may be simplified. In addition, it may be easier to clean a wearable article which has fewer electronic components attached thereto or incorporated therein. Furthermore, the removable electronic module may be easier to maintain and/or troubleshoot than embedded electronics. The electronic module may comprise flexible electronics such as a flexible printed circuit (FPC). The electronic module may be configured to be electrically coupled to the wearable article.

It may be desirable to avoid direct contact of the electronic module with the wearer's skin while the wearable article is being worn. In particular, it may be desirable to avoid the electronic module coming into contact with sweat or moisture on the wearer's skin. The electronic module may be provided with a waterproof coating or waterproof casing. For example, the electronic module may be provided with a silicone casing. It may further be desirable to provide a pouch or pocket in the garment to contain the electronic module in order to prevent chafing or rubbing and thereby improve comfort for the wearer. The pouch or pocket may be provided with a waterproof lining in order to prevent the electronic module from coming into contact with moisture.

The master device 20 may comprise a power source. The power source may comprise a plurality of power sources. The power source may be a battery. The battery may be a rechargeable battery. The battery may be a rechargeable battery adapted to be charged wirelessly such as by inductive charging. The power source may comprise an energy harvesting device. The energy harvesting device may be configured to generate electric power signals in response to kinetic events such as kinetic events performed by a wearer of the wearable article. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of the wearable article. The energy harvesting device may be a thermoelectric energy harvesting device. The power source may be a super capacitor, or an energy cell.

The master device 20 may comprise a communicator. The communicator may be a mobile/cellular communicator operable to communicate the data wirelessly via one or more base stations. The communicator may provide wireless communication capabilities for the garment and enables the garment to communicate via one or more wireless communication protocols such as used for communication on: a wireless wide area network (WWAN), a wireless metroarea network (WMAN), a wireless local area network (WLAN), a wireless personal area network (WPAN), a near field communication (NFC), and a cellular communication network. The cellular communication network may be a fourth generation (4G) LTE, LTE Advanced (LTE-A), fifth generation (5G), sixth generation (6G), and/or any other present or future developed cellular wireless network. A first communicator of the master device 20 may be provided for cellular communication and a separate communicator may be provided for short-range local communication over WLAN, WPAN, NFC, or Bluetooth®, WiFi or any other electromagnetic RF communication protocol.

The master device 20 may comprise a Universal Integrated Circuit Card (UICC) that enables the wearable article to access services provided by a mobile network operator (MNO). The UICC may include at least a read-only memory (ROM) configured to store an MNO profile that the wearable article can utilize to register and interact with an MNO. The UICC may be in the form of a Subscriber Identity Module (SIM) card. The wearable article may have a receiving section arranged to receive the SIM card. In other examples, the UICC is embedded directly into a controller of the wearable article. That is, the UICC may be an electronic/embedded UICC (eUICC). A eUICC is beneficial as it removes the need to store a number of MNO profiles, i.e. electronic Subscriber Identity Modules (eSIMs). Moreover, eSIMs can be remotely provisioned to garments. The wearable article may comprise a secure element that represents an embedded Universal Integrated Circuit Card (eUICC).

The bidirectional line may be formed from a conductive thread or wire. The conductor may be incorporated into the wearable article. The conductor may be an electrically conductive track or film. The conductor may be a conductive transfer. The conductor may be formed from a fibre or yarn of the textile. This may mean that an electrically conductive materials are incorporated into the fibre/yarn.

Figure 4:
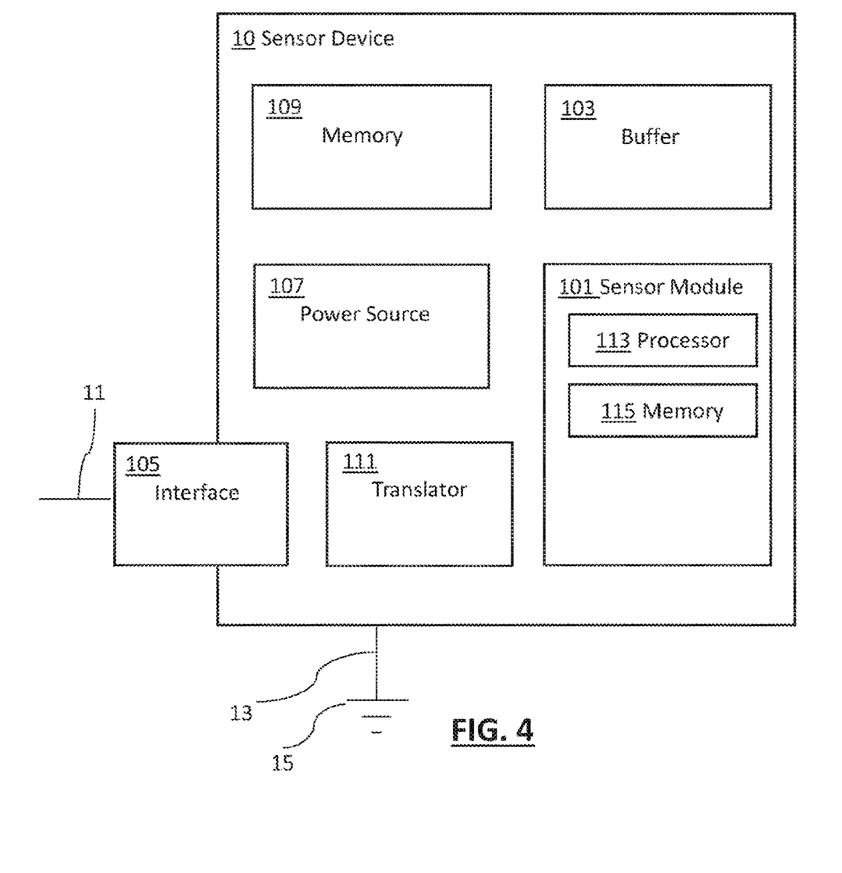
FIG. 4 shows a schematic diagram for another example sensor device according to aspects of the present disclosure.

Referring to FIG. 4, there is shown another example sensor device 10 according to aspects of the present disclosure. The sensor device 10 has a similar structure to the sensor device 10 of FIG. 1, and like reference numerals are used to indicate like components. In the example of FIG. 4, the sensor module 101 comprises a processor 113 and a memory 115. The memory 115 stores instructions and data. The instructions when executed by the processor 113 cause the processor 113 to perform operations.

These operations comprise the processor 113 generating a compressed representation of data sensed by the sensor module 101. The compressed representation of the data may be transmitted to a master device over the single-wire bidirectional line 11 using the I/O interface 105. In these implementations, when the master device 20 requests data over the single-wire bidirectional line 11, the sensor device 10 transmits a compressed representation of recent data sensed by the sensor module 101. Meanwhile, the data sensed by the sensor module 101 may be stored in the buffer 103. In this way, the master device 20 obtains a current representation of the data sensed by the sensor module 101 but the original time-series data sensed by the sensor module 101 is preserved in the buffer 103. Beneficially, transmitting a compressed representation of recent data sensed by the sensor module 101 enables the fast transmission of data to the master device 20 for real-time or near real-time applications, while retaining the original sensed data for later analysis. The compressed representation of the data may be determined from data sensed by the sensor module 101 over a defined time window. The length of the time window may be selected as appropriate by the person skilled in the art. In some examples, the length of the window is between 1 and 255 samples.

The compressed representation of the data may be an inference generated from data sensed by the sensor module 101. The inference generated by employing a machine-learned model stored on the memory 115 of the sensor module 101. The generated inference may be transmitted to a master device over the single-wire bidirectional line 11 using the I/O interface 105. The data sensed by the sensor module 101 may be stored on the buffer 103. Beneficially, this arrangement enables the master device 20 to obtain an inference for real-time or near-real time analysis, while retaining the original sensed data in the buffer for later retrieval and analysis. In examples where the sensor module comprises a motion sensor, the inference may relate to activity recognition, fitness activity recognition, motion intensity detection, or vibration intensity detection amongst others. The inference may be generated from data sensed by other sensors external to the sensor device 10.

The machine-learned model may be or otherwise include various machine-learned models such as decision trees, artificial neural networks (e.g. deep neural networks) or other types of machine-learned models, including non-linear models and/or linear models. Neural networks can include feed-forward neural networks, recurrent neural networks (e.g. long short-term memory recurrent neural networks), convolutional neural networks or other forms of neural networks. Other examples of machine-learned models include Bayesian networks and Naïve Bayes networks. Other example machine-learned models/algorithms that may be used within the scope of the present disclosure include support vector machine techniques, Gaussian mixture models, hidden Markov models, and genetic algorithms. Of course, other machine learning techniques as known to the skilled person may be used in the context of the present disclosure.

The processor 113 may comprise a signal processing module arranged to pre-process the data sensed by the sensor module 101 prior to generating the inference. Data sensed by sensor modules 101 are typically affected by noise and changes in physical conditions. This can be a particular problem for wearable articles due to factors such as reduced size, battery life, hardware considerations, and poor skin contact. The configuration of the sensor modules 101, differences in timing measurements, and the technical limitations of the sensor modules 101 can introduce noise and errors into the obtained data. The signal processing module pre-processes the data so as to reduce nose, errors, optionally normalize the data, and generally prepare the data for the feature extraction process. The use of specific pre-processing techniques greatly depends on the domain and the scenario. Example techniques include normalization, smoothing, interpolation, or segmentation or a combination thereof.

The processor 113 may comprise a feature extraction module. The feature extraction module may extract a feature set from the processed data. This process may be considered as an extraction and selection process whereby a plurality of features are extracted from the processed data and the most significant of these features are then selected to form the extracted feature set. Feature extraction is aimed at reducing the noise, redundancy, and dimensionality of the processed data so that only significant information remains. This means that the employed machine-learned model uses only the most significant information from the data. With feature extraction, data can be compared to others in the time, frequency, and other domains defined by the extracted features. The feature extraction module may use a domain-driven approach to extract features from the processed data. Additionally or separately, the feature extraction module may use an automatic driven approach to extract features from the processed data. Example features include the mean, variance, energy, peak-to-peak, zero-crossing, positive zero-crossing, negative zero-crossing, peaks, positive peaks, negative peaks, minimums and maximums.

Not all of the features extracted by the feature extraction module may be relevant or useful for the machine-learned model. Some of the extracted features may even be redundant or misleading. Further, the number of extracted features generally determines the computational cost of the machine-learning process. To this end, once the features have been extracted by the feature extraction module, the feature extraction module may perform a feature selection process to reduce the size of the feature set used in the subsequent recognition operation. Feature selection approaches generally iterate through the extracted features to obtain the best set of extracted features to represent the data. The feature extraction module may use a principal component analysis (PCA) based procedure to reduce the dimensionality of the extracted feature set. The feature extraction module may use a linear discriminant analysis (LDA) based procedure to reduce the dimensionality of the extracted feature set. The feature extraction module is not limited to the use of PDA or LDA to reduce the dimensionality of the extracted feature set. Other selection techniques as known by the skilled person such as mutual information, correlation and fast correlation may be used as appropriate.

In some examples, the sensor device 10 may receive updated machine-learned model data over the single-wire bidirectional line 11. The updated machine-learned model data may be used to update the machine-learned model stored on the memory 115 or replace the machine-learned model stored on the memory. The updated machine-learned model data may be transmitted by a master device.

Figures 5, 6:
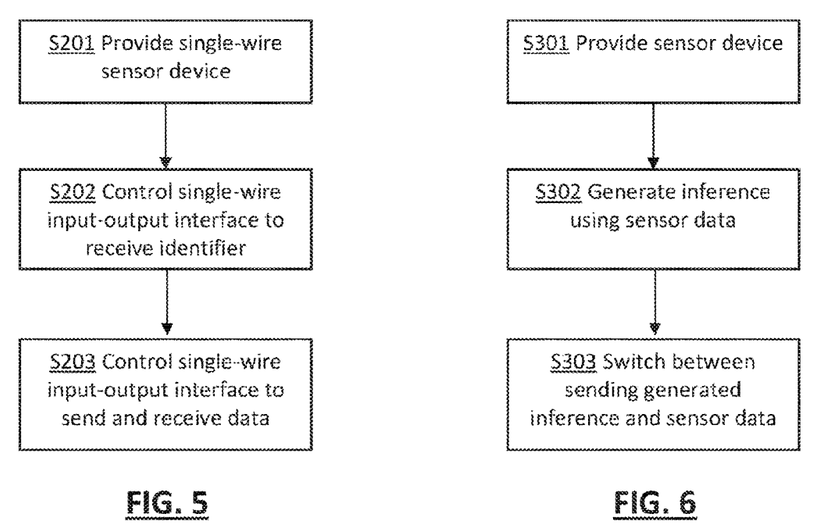
FIG. 5 shows a flow diagram for another example method according to aspects of the present disclosure.
FIG. 6 shows a flow diagram for yet another example method according to aspects of the present disclosure.

Referring to FIG. 5, there is shown a flow diagram for an example method according to aspects of the present disclosure. Step S201 of the method comprises providing a single-wire sensor device comprising a sensor module, a programmable and erasable non-volatile memory, and a single-wire input-output interface. Step S202 of the method comprises controlling the single-wire input-output interface to receive an identifier over a single-wire bidirectional line and write the identifier to the programmable and erasable non-volatile memory. Step S203 of the method comprises controlling the single-wire input-output interface to send and receive data over the single-wire bidirectional line.

Referring to FIG. 6, there is shown a flow diagram for an example method according to aspects of the present disclosure. Step S301 of the method comprises providing a sensor device. Step S302 of the method comprises generating an inference using data sensed by a sensor module of the sensor device. Step S303 of the method comprises controlling the sensor device to switch between sensing data sensed by the sensor module and the inference generated by the sensor over a bidirectional line via the input-output interface.

Figure 7:
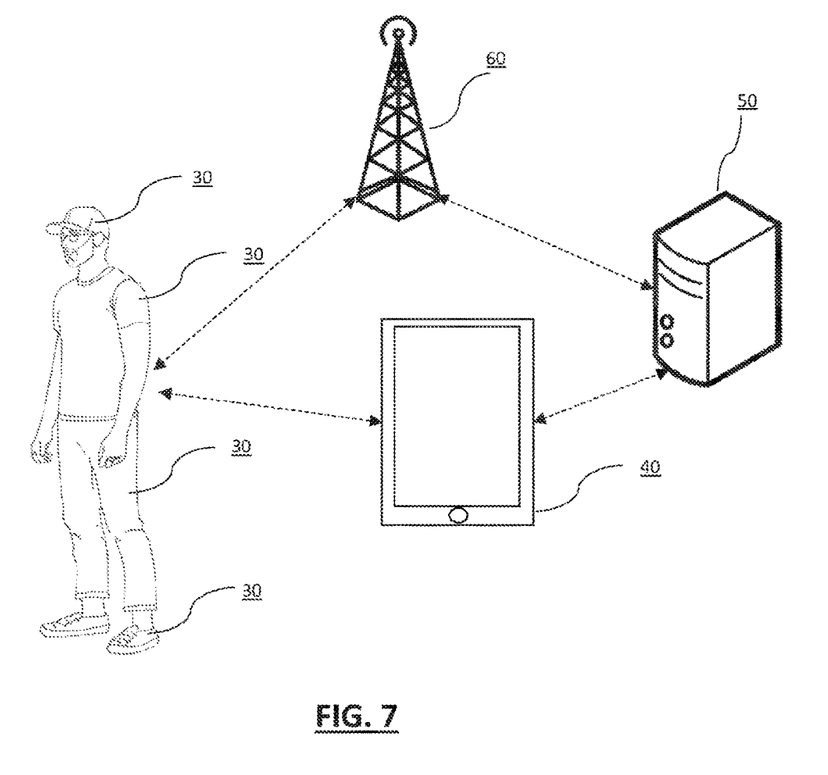
FIG. 7 shows a schematic diagram for another example system according to aspects of the present disclosure.

Referring to FIG. 7, there is shown an example system according to aspects of the present disclosure. The system comprises a plurality of wearable articles 30 worn by a user. The plurality of wearable articles 30 are garments and in particular a top, bottoms, headwear and footwear.

The plurality of wearable articles 30 comprise the system of FIG. 3. That is, the wearable articles 30 comprise a master device and a plurality of sensor devices connected together and communicating over a single-wire bidirectional line. The master device comprises a communicator and is arranged to transmit data to a user electronic device 40 over a short-range wireless communication protocol. In addition, the communicator is arranged to transmit data to the server 50 over a cellular communication protocol represented by base station 60. The user electronic device 40 and server 50 are also able to communication over a wireless or wired communication network.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A system comprising:
   a master device;
   a sensor device comprising:
      a sensor module comprising a processor and a memory;
      a buffer that stores time-series sensor data sensed by the sensor module; and
      an input-output interface that connects the sensor device to the master device over a bidirectional line, sends data to the master device over the bidirectional line and receives data from the master device over the bidirectional line,
   wherein the processor loads a model from the memory and generates an inference using the model and the time-series data stored in the buffer, and
   wherein the sensor device switches between sending to the master device, over the bidirectional line via the input-output interface, the time-series sensor data stored in the buffer and the generated inference based on a command received from the master device over the bidirectional line.

2. The system as claimed in claim 1, wherein the model is a machine-learned model, and the sensor device is arranged to receive an update to the machine-learned model over the input-output interface.

3. The system as claimed in claim 1, wherein the input-output interface is a single-wire input-output interface.

4. The system as claimed in claim 1, wherein the sensor device is arranged to receive power via the input-output interface.

5. The system as claimed in claim 1, further comprising a power source arranged to supply power to the sensor device.

6. The system as claimed in claim 5, wherein the sensor device is arranged to receive power over the input-output interface and store the power in the power source.

7. The system as claimed in claim 5, wherein the power source comprises a capacitor, optionally a supercapacitor.

8. The system as claimed in claim 5, wherein the power source comprises a rechargeable battery.

9. The system as claimed in claim 1, further comprising a non-volatile memory arranged to store an identifier for the sensor device.

10. The system as claimed in claim 9, wherein the memory is an erasable and programmable non-volatile memory.

11. The system as claimed in claim 10, wherein the input-output interface is arranged to receive an identifier over the bidirectional line and write the identifier to the erasable and programmable memory.

12. The system as claimed in claim 9, wherein the input-output interface is arranged to receive an identifier over the bidirectional line, and wherein the sensor device is arranged to compare the received identifier to an identifier stored in the non-volatile memory.

13. The system as claimed in claim 1, wherein the sensor module comprises one or more biosensor modules.

14. A method comprising:
   providing a master device;
   providing a sensor device comprising:
      a sensor module;
      a buffer; and
      an input-output interface that connects the sensor device to the master device over a bidirectional line, sends data to the master device over the bidirectional line and receives data from the master device over the bidirectional line, wherein the sensor module comprises a processor and a memory
   storing, by the sensor module, time-series sensor data in the buffer;
   loading, by the processor, a model from the memory;
   generating, by the processor, an inference using the model and the time-series sensor data stored in the buffer;
   switching between sending to the master device, over the bidirectional line via the input-output interface, the time-series sensor data stored in the buffer and the generated inference based on a command received from the master device over the bidirectional line.

15. The system as claimed in claim 1, wherein the sensor module is a motion sensor module comprising at least one of an accelerometer and a gyroscope, and wherein the generated inference is an activity classification.

* * * * *